United States Patent
Trieu

(10) Patent No.: US 8,945,224 B2
(45) Date of Patent: Feb. 3, 2015

(54) SACRO-ILIAC IMPLANT SYSTEM, METHOD AND APPARATUS

(75) Inventor: Hai H. Trieu, Cordova, TN (US)

(73) Assignee: Warsaw, Orthopedic, Inc., Warsaw, IN (US)

( * ) Notice: Subject to any disclaimer, the term of this patent is extended or adjusted under 35 U.S.C. 154(b) by 724 days.

(21) Appl. No.: 12/726,886

(22) Filed: Mar. 18, 2010

(65) Prior Publication Data
US 2011/0230966 A1    Sep. 22, 2011

(51) Int. Cl.
*A61F 2/44*        (2006.01)
*A61B 17/56*       (2006.01)
*A61B 17/70*       (2006.01)

(52) U.S. Cl.
CPC .......... *A61B 17/562* (2013.01); *A61B 17/7055* (2013.01)
USPC ....................................... 623/17.12

(58) Field of Classification Search
USPC ............................ 623/17.11, 17.12
See application file for complete search history.

(56) References Cited

U.S. PATENT DOCUMENTS

| | | | |
|---|---|---|---|
| 6,053,916 A | 4/2000 | Moore | |
| 6,620,196 B1 | 9/2003 | Trieu | |
| 6,733,531 B1 | 5/2004 | Trieu | |
| 6,869,445 B1 * | 3/2005 | Johnson | 623/17.11 |
| 6,893,466 B2 | 5/2005 | Trieu | |
| 6,899,719 B2 | 5/2005 | Reiley et al. | |
| 6,974,479 B2 | 12/2005 | Trieu | |
| 7,445,634 B2 | 11/2008 | Trieu | |
| 7,534,268 B2 * | 5/2009 | Hudgins et al. | 623/17.12 |
| 7,593,777 B2 * | 9/2009 | Gerber | 607/115 |
| 7,931,689 B2 * | 4/2011 | Hochschuler et al. | 623/17.12 |
| 2002/0068974 A1 * | 6/2002 | Kuslich et al. | 623/17.11 |
| 2004/0073308 A1 * | 4/2004 | Kuslich et al. | 623/17.11 |
| 2004/0106924 A1 * | 6/2004 | Ralph et al. | 606/71 |
| 2004/0215343 A1 * | 10/2004 | Hochschuler et al. | 623/17.12 |
| 2005/0015148 A1 * | 1/2005 | Jansen et al. | 623/17.11 |
| 2005/0209595 A1 * | 9/2005 | Karmon | 606/76 |
| 2005/0261781 A1 * | 11/2005 | Sennett et al. | 623/23.54 |
| 2006/0047341 A1 | 3/2006 | Trieu | |
| 2006/0085002 A1 | 4/2006 | Trieu et al. | |
| 2006/0095134 A1 | 5/2006 | Trieu et al. | |
| 2006/0106382 A1 | 5/2006 | Gournay et al. | |
| 2006/0149379 A1 * | 7/2006 | Kuslich et al. | 623/17.12 |
| 2006/0161154 A1 | 7/2006 | McAfee | |
| 2006/0182780 A1 * | 8/2006 | Riley et al. | 424/426 |
| 2007/0021801 A1 | 1/2007 | Heruth et al. | |
| 2007/0100355 A1 * | 5/2007 | Bonde et al. | 606/108 |
| 2007/0135922 A1 * | 6/2007 | Trieu | 623/17.12 |
| 2007/0142842 A1 | 6/2007 | Krueger et al. | |
| 2007/0213660 A1 | 9/2007 | Richards et al. | |
| 2007/0255406 A1 * | 11/2007 | Trieu | 623/17.11 |
| 2007/0265621 A1 | 11/2007 | Matthis et al. | |
| 2007/0298068 A1 * | 12/2007 | Badawi et al. | 424/423 |
| 2008/0009861 A1 | 1/2008 | Stark | |
| 2008/0021463 A1 | 1/2008 | Georgy | |
| 2008/0039843 A1 | 2/2008 | Abdou | |
| 2008/0086133 A1 * | 4/2008 | Kuslich et al. | 606/61 |
| 2008/0154306 A1 | 6/2008 | Heinz | |

(Continued)

*Primary Examiner* — Christian Sevilla

(57) ABSTRACT

A sacro-iliac implant system includes at least one implant including a body defining an outer surface and being disposed to space apart opposing articular surfaces of a sacro-iliac joint. The body is engageable with the opposing articular surfaces and the outer surface is compliant to a configuration of the opposing articular surfaces such that the body facilitates relative movement of the opposing articular surfaces. Methods of use are disclosed.

20 Claims, 5 Drawing Sheets

(56) References Cited

U.S. PATENT DOCUMENTS

| | | |
|---|---|---|
| 2008/0243249 A1* | 10/2008 | Kohm et al. ............... 623/17.12 |
| 2009/0024174 A1 | 1/2009 | Stark |
| 2009/0076517 A1 | 3/2009 | Reiley et al. |
| 2009/0082705 A1* | 3/2009 | Asfora ............................ 601/46 |
| 2009/0093817 A1 | 4/2009 | Zucherman et al. |
| 2009/0099610 A1 | 4/2009 | Johnson et al. |
| 2009/0149860 A1 | 6/2009 | Scribner et al. |
| 2009/0181892 A1 | 7/2009 | Thorne et al. |
| 2009/0216238 A1 | 8/2009 | Stark |
| 2009/0263321 A1 | 10/2009 | McDonald et al. |
| 2009/0263459 A1 | 10/2009 | King et al. |
| 2009/0264489 A1 | 10/2009 | Hildebrand et al. |
| 2009/0264490 A1 | 10/2009 | Zanella et al. |
| 2009/0264491 A1 | 10/2009 | McKay et al. |
| 2011/0098816 A1* | 4/2011 | Jacob et al. ................ 623/17.11 |
| 2011/0098817 A1* | 4/2011 | Eckhardt et al. ........... 623/17.11 |

* cited by examiner

SACRO-ILIAC IMPLANT SYSTEM, METHOD AND APPARATUS

TECHNICAL FIELD

The present disclosure generally relates to medical devices for the treatment of musculoskeletal disorders, and more particularly to an implant system and method for treating the sacro-iliac joint.

BACKGROUND

The sacro-iliac joint is a diarthrodial joint that joins the sacrum to the ilium bones of the pelvis. In the sacro-iliac joint, the sacral surface has hyaline cartilage that moves against fibrocartilage of the iliac surface. The spinal column is configured so that the weight of an upper body rests on the sacro-iliac joints at the juncture of the sacrum and ilia. Stress placed on the sacro-iliac joints in an upright position of the body makes the lower back susceptible to injury.

Disorders of the sacro-iliac joint can cause low back and radiating buttock and leg pain in patients suffering from degeneration and laxity of the sacro-iliac joint. In some cases, the sacro-iliac joint can undergo dehydration and destabilization, similar to other cartilaginous joints, which causes significant pain. The sacro-iliac joint is also susceptible to trauma and degeneration, from fracture and instability. It is estimated that disorders of the sacro-iliac joint are a source of pain for millions of people suffering from back and radicular symptoms.

Non-surgical treatments, such as medication, injection, mobilization, rehabilitation and exercise can be effective, however, may fail to relieve the symptoms associated with these disorders. Surgical treatment of these disorders includes stabilization and/or arthrodesis. Stabilization can include the use of bone screws that are directly threaded into bone. Arthrodesis may include immobilization of a joint. The present disclosure describes an improvement over these prior art technologies.

SUMMARY OF THE INVENTION

Accordingly, an implant system and method is provided for treating the sacro-iliac joint. It is contemplated that the system may include an implant configured for disposal with the sacro-iliac joint. It is further contemplated that the implant system and method may be employed for an arthroplasty treatment.

In one particular embodiment, in accordance with the principles of the present disclosure, a sacro-iliac implant system is provided. The sacro-iliac implant system includes at least one implant including a body defining an outer surface and being disposed to space apart opposing articular surfaces of a sacro-iliac joint. The body is engageable with the opposing articular surfaces and the outer surface is compliant to a configuration of the opposing articular surfaces such that the body facilitates relative movement of the opposing articular surfaces.

In one embodiment, the sacro-iliac implant system includes a bio-compatible material. At least one implant including a body defining an outer surface is configured to engage and space apart opposing articular surfaces of a sacro-iliac joint to facilitate relative movement of the opposing articular surfaces. The body is configured to expand from a first, collapsed orientation to a second inflated orientation whereby the outer surface is compliant to a configuration of the opposing articular surfaces such that the body is inflated with the fluid and moldable in situ to the configuration of the opposing articular surfaces. A delivery instrument is configured to deliver the fluid to the body. The instrument is detachably connected with the body.

In one embodiment, a method for treating a sacro-iliac joint is disclosed. The method includes the steps of: providing at least one implant, similar to those described; providing a delivery instrument configured to deliver a bio-compatible material to the body; delivering the body to the sacro-iliac joint between the opposing articular surfaces with the delivery instrument; disposing the body between the opposing articular surfaces such that the body spaces apart the opposing articular surfaces and the outer surface is compliant to a configuration of the opposing articular surfaces to facilitate relative movement of the opposing articular surfaces; and removing the delivery instrument from the sacro-iliac joint.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
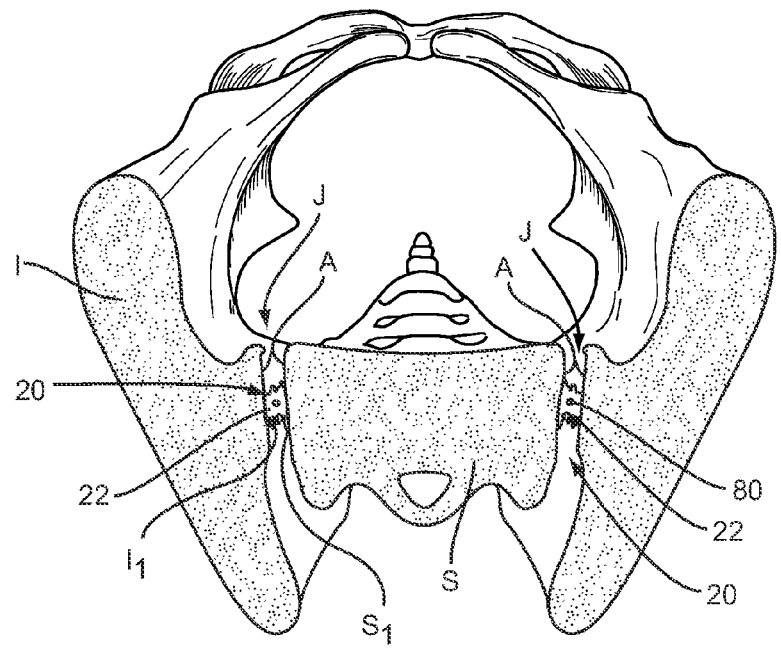
FIG. 1 is a plan view, in part cross section, of one particular embodiment of an implant system in accordance with the principles of the present disclosure and a sacro-iliac/ilio-pelvic region.

The exemplary embodiments of the implant system and methods of use disclosed are discussed in terms of medical devices for treating the sacro-iliac joint. It is envisioned that the implant system and methods of use disclosed provide stability and maintain structural integrity while reducing stress on the sacro-iliac joint. It is further envisioned that the present disclosure may be employed to treat musculoskeletal disorders including sacro-Iliac dysfunction or syndrome, dehydration, destabilization, laxity, fracture, tumor, spinal disorders and other orthopedic disorders. It is contemplated that the present disclosure may be employed with surgical treatments, including open surgery, percutaneous and minimally invasive procedures of such disorders, such as, for example, arthroplasty to maintain motion, bone graft and implantable prosthetics. It is further contemplated that the present disclosure may be employed with other osteal and bone related applications, including those associated with diagnostics and therapeutics. The disclosed implant system and methods may be employed in a surgical treatment with a patient in a prone or supine position, employing a posterior, lateral, inferior, posterior-inferior, superior or anterior approach. The present disclosure may be employed with procedures for treating the lumbar, cervical, thoracic and pelvic regions of a spinal column.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of an implant system, related components and exemplary methods of employing the implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there are illustrated components of the implant system in accordance with the principles of the present disclosure.

The components of the implant system are fabricated from materials suitable for medical applications, including metals, synthetic polymers, ceramics, bone, bio-compatible materials and/or their composites, depending on the particular application and/or preference of a medical practitioner. For example, components of the implant system, such as, for example, an implant body, an outer surface of the implant body and/or portions thereof, which may be monolithically formed or integrally connected and/or instruments and/or expanding devices, discussed below, can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO$_4$ composites, ceramics and composites thereof such as calcium phosphate (e.g. SKELITE™ manufactured by Biologix Inc.), rigid polymers including polyphenylene, polyamide, polyimide, polyetherimide, polyethylene, polyurethanes of any durometer, epoxy and silicone. Different components of the implant system may have alternative material composites to achieve various desired characteristics such as strength, rigidity, elasticity, compliance, biomechanical performance, durability and radiolucency or imaging preference. The components of the implant system may also be fabricated from a heterogeneous material such as a combination of two or more of the above-described materials.

It is envisioned that the components of the implant system can be manufactured via various methods. For example, the implant body can be manufactured and assembled via injection-molding, insert-molding, overmolding, compression molding, transfer molding, co-extrusion, pultrusion, dip-coating, spray-coating, powder-coating, porous-coating, milling from a solid stock material, and their combinations. One skilled in the art, however, will realize that such materials and fabrication methods suitable for assembly and manufacture, in accordance with the present disclosure, would be appropriate.

The implant system includes an orthopedic implant, such as, for example, a sacro-iliac implant 20, which is configured, for example, to treat sacro-iliac joint disorders including those caused by degeneration or trauma. It is contemplated that sacro-iliac implant 20 may be employed for arthroplasty applications, as will be described.

Sacro-iliac implant 20 includes a body 22. Body 22 has an outer surface 24 configured as a compliant balloon that is elongated along a longitudinal axis a thereof. Outer surface 24 has an expandable configuration and defines an inner cavity 25. Outer surface 24 is expandable and configured for radial expansion corresponding to an increasing volume of inner cavity 25. Outer surface 24 is configured to expand from a first, collapsed orientation (FIGS. 1, 2 and 3) to a second inflated orientation (FIGS. 4, 5 and 6) such that outer surface 24 engages opposing articular surfaces A of a sacro-iliac joint J.

Body 22 is disposed within sacro-iliac joint J to space apart opposing articular surfaces A. Outer surface 24 is compliant to a configuration of opposing articular surface A, as will be described, such that body 22 facilitates relative movement of opposing articular surfaces A. It is contemplated that body 22 may be elastically deformable or plastically deformable. It is further contemplated that outer surface 24 may be slidably engaged, fixed and/or releasable engageable with particular surfaces A.

It is envisioned that body 22 is initially disposed in a relatively smaller cross-sectional dimension, for example, diameter, height and/or width, which may include a first orientation such as, for example, a collapsed or pre-deployed orientation. It is further envisioned that outer surface 24 can be expanded or deployed in situ such that a cross-sectional dimension of body 22 is increased and outer surface 24 is secured within sacro-iliac joint J. It is contemplated that outer surface 24 is expandable in one or a plurality of dimensions, such as, for example, height, width, length, diameter, radial direction and/or volumetric direction. In one embodiment, expansion of implant 20 is reversible for removal and/or revision.

It is contemplated that articular surface A may refer to a sacral surface $S_1$ of a sacrum S and/or an iliac surface $I_1$ of an ilium I. Outer surface 24 is configured to engage opposing articular surfaces such as sacral surface $S_1$ and iliac surface $I_1$ and/or opposing valleys or peaks of an individual sacrum S or ilium I. Body 22 may expand to a hollow, porous or cage configuration. Outer surface 24 is compliant to articular surfaces A and has a continuously even or smooth configuration. It is contemplated that outer surface 24 has a compliant configuration to substantially match articular surface(s) A and/or may be substantially smooth, rough, textured, spiked, porous, semi-porous, permeable, semi-permeable, impermeable, dimpled, keeled and/or polished.

Body 22 extends from a first end 26 to a second end 28. Body 22 has a first diameter $d_1$ (FIG. 3) in the first non-expanded orientation and a second diameter $d_2$ (FIG. 6) in the expanded orientation, according to the requirements of the particular application. As outer surface 24 expands to the expanded orientation, outer surface 24 is compliant such that body 22 is moldable in situ to the configuration of opposing articular surfaces A.

Figure 4:
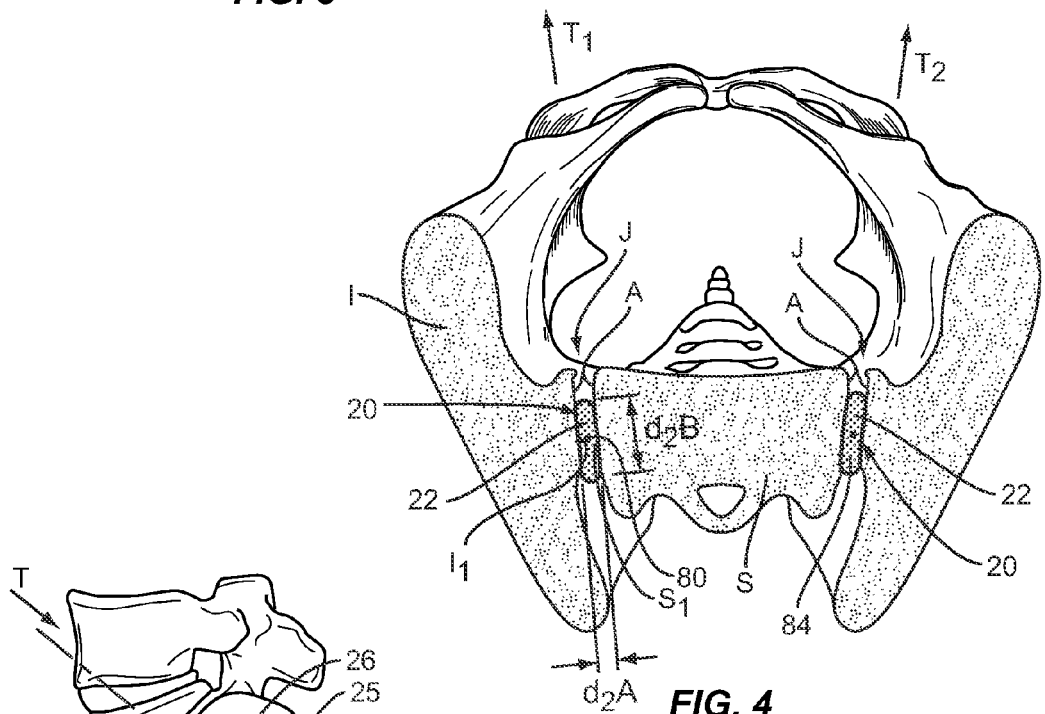
FIG. 4 is a plan view, in part cross section, of the implant system and the region shown in FIG. 1.

Outer surface 24 is configured to expand to non-uniform diameter $d_2$ in a plurality of directions, which includes, for example, diameter $d_2A$ and diameter $d_2B$, as shown in FIG. 4. Outer surface 24 expands to diameter $d_2A$ in a direction perpendicular to articular surfaces A to space apart articular surfaces A. Outer surface 24 also expands to diameter $d_2B$ in a direction parallel to articular surfaces A, along articular surfaces A, to increase the amount of joint surface area contacted by outer surface 24. Expansion of outer surface 24 to diameter $d_2B$ provides an increased contact area to improve joint surface support. It is contemplated that outer surface 24 can be expanded to a maximum pressure for the compliant balloon.

Body 22 is molded in situ via delivery of a curable, biocompatible material to inner cavity 25, that inflates outer surface 24 with a sufficient amount of fluid to fill the targeted space between opposing articular surfaces A within sacro-iliac joint J, as will be described. The fluid is initially flowable so that it can be injected and/or extruded into inner cavity 25. Upon inflation of outer surface 24 to the expanded orientation, the fluid changes from a liquid to a relatively solid non-flowable form having a significantly higher modulus of elasticity relative to the initial fluid form, to mold body 22 in situ.

It is envisioned that molding of body 22 in the expanded orientation can include setting, solidification, a significant increase in viscosity or modulus of elasticity of the fluid, cross-linking, polymerization and/or vulcanization of the fluid. Outer surface 24 may be inflated with flowable and moldable bio-compatible materials, such as, for example, fluid precursors to silicone based materials, polyurethanes, hydrogels, synthetic rubbers and elastomers, epoxy, and/or polymenthylmethaerylate (PMMA), polyolefin, silicone polyurethane co-polymers and/or combinations thereof.

It is envisioned that diameter $d_1$ may be in a range of approximately 1-20 millimeters (mm), and preferably in a range of 2-10 mm. It is further envisioned that diameter $d_1$ may be varied depending on whether an sacro-iliac joint is drilled and/or tapped before insertion of an implant. It is contemplated that diameter $d_2$ may be in a general range of approximately 2-50 mm. For example, diameter $d_2A$ may be in a range of approximately 2-15 mm, and preferably in a range of 2-10 mm. Diameter $d_2B$ may be in a range of approximately 5-50 mm, and preferably in a range of 10-40 mm. Outer surface 24 may expand to diameter $d_2B$ in one or a plurality of directions. It is further contemplated that diameter $d_2$ may be varied depending on the cross section of body 22.

Upon molding in situ, body 22 is flexible and resilient, and separates articular surfaces A to dilate the sacro-iliac joint, facilitate relative movement of opposing articular surfaces A, and/or prevent joint surfaces from undesired engagement such as that caused by degeneration and cartilage wear. It is contemplated that such spacing apart of the articular surfaces of the sacro-iliac joint with compliant, molded body 22, tensions ligaments, supports the sacro-iliac joint and restores motion of the sacro-iliac joint. It is further contemplated that the overall and/or cross-sectional geometry of expanded outer surface 24 may have various configurations, for example, round, oval, oblong, triangular, rectangular, polygonal, irregular, uniform, non-uniform, consistent or variable, according to the geometry of the joint space disposed between the articular surfaces and/or the requirements of a particular implant system application. It is envisioned that body 22 may be solid, permeable, semi-permeable, impermeable, porous and/or semi-porous.

It is envisioned that outer surface 24 can be expanded to various configurations and dimensions with regard to size, shape, thickness, geometry and material. Body 22 may also be formed of one or a plurality of elements such as spaced apart portions, staggered patterns and mesh. It is envisioned that the particular geometry and material parameters of body 22 may be selected to modulate the flexibility or stiffness of sacro-iliac implant 20, such as those examples discussed herein. For example, body 22 can be configured to have varying ranges or degrees of flexibility or stiffness such as rigid, compliant, or reinforced. Depending on the flexibility or stiffness of body 22, the flexibility or stiffness of sacro-iliac implant 20 can be contoured according to the requirements of a particular application. It is contemplated that the ability to vary stiffness of sacro-iliac implant 20 provides restoration of kinematic function of joint J. It is envisioned that the components of sacro-iliac implant 20 may be monolithically formed, integrally connected or arranged with attaching elements.

In one embodiment, body 22 may be molded in situ to form one or a plurality of cavities, which may partially extend or completely extend through body 22. Such cavities can be oriented with body 22 to face articular surfaces A, sacral surface $S_1$ and iliac surface $I_1$. It is further envisioned that the cavities may include through holes, slots, voids, indentations, and/or non-interference configurations and dimensions.

In one embodiment, body 22 and the cavities described above may be configured to expel and/or elute at least one agent therefrom. The agent can be configured as drug depots with medication for pain and may include antibiotics and/or therapeutics. It is contemplated that body 22 and/or each of the cavities may include one or a plurality of agents.

It is envisioned that the active agents may include one or a plurality of therapeutic agents and/or pharmacological agents for release, including sustained release, into sacro-iliac joint J to treat, for example, pain, inflammation and degeneration. The agents may include pharmacological agents, such as, for example, antibiotics, pain medications, analgesics, anesthetics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, clonidine, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It is envisioned that body 22 and/or the cavities described above are capable of accepting at least one agent before, during and/or after implantation with joint J, and/or delivery in vivo of the agent to tissues of joint J and tissues surrounding joint J, including bone. Body 22 and the cavities described above may be replenished, via one or a plurality of iterations, with therapeutic and/or pharmacological agents.

In one embodiment, the implant system includes a plurality of bodies 22, described above, in each or both sacro-iliac joints. It is contemplated that employing the plurality of bodies 22 can optimize the amount sacro-iliac joint J can be spaced apart such that a joint space dimension can be preselected. The plurality of bodies 22 can be inserted through the same or an alternate trajectory. The plurality of bodies 22 can be oriented in a side by side engagement, spaced apart and/or staggered. It is envisioned that one or all of the plurality of bodies 22 may be inserted via a trajectory oriented from an anterior, posterior, superior or inferior direction, similar to that described herein. It is further envisioned that one or a plurality of bodies 22 may be used.

In assembly, operation and use, the implant system including sacro-iliac implant 20 is employed with a surgical procedure for treatment of a sacro-iliac joint J of a patient, as discussed herein. The implant system may also be employed with other surgical procedures. In particular, the implant system is employed with a surgical arthroplasty procedure for treatment of an applicable condition or injury of an affected sacro-iliac joint J, as shown in FIGS. 1-6. It is contemplated that the implant system is inserted with sacro-iliac joint J to space apart articular joint surfaces, establish joint tension, provide support and relative motion of the articular surfaces of sacro-iliac joint J in a less invasive approach for treatment. It is further contemplated that the implant system is inserted with a sacro-iliac joint J as a sacro-iliac joint spacer to restore ligamentous tension, eliminate painful motion, and/or preserve and restore motion and/or separate and cushion opposing articulating surfaces. It is envisioned that the implant system may maintain joint tension without promoting bone growth. Diagnostic testing may be performed to confirm a sacro-iliac joint disorder, including pain, and the requirement for treatment.

In use, to treat the affected section of sacro-iliac joint J, a medical practitioner obtains access to a surgical site including sacro-iliac joint J in any appropriate manner, such as through incision and retraction of tissues. It is envisioned that the implant system may be used in any existing surgical method or technique including open surgery, mini-open surgery, minimally invasive surgery and percutaneous surgical implantation, whereby sacro-iliac joint J is accessed through a mini-incision, or sleeve that provides a protected passageway to the area. Once access to the surgical site is obtained, the particular surgical procedure is performed for treating the sacro-iliac joint disorder. The implant system is then employed to augment the surgical treatment. The implant system can be delivered or implanted as a pre-assembled device or can be assembled in situ. The implant system may be completely or partially revised, removed or replaced in situ. It is contemplated that one or all of the components of the implant system can be delivered to the surgical site via manual manipulation and/or a free hand technique.

Figure 2:
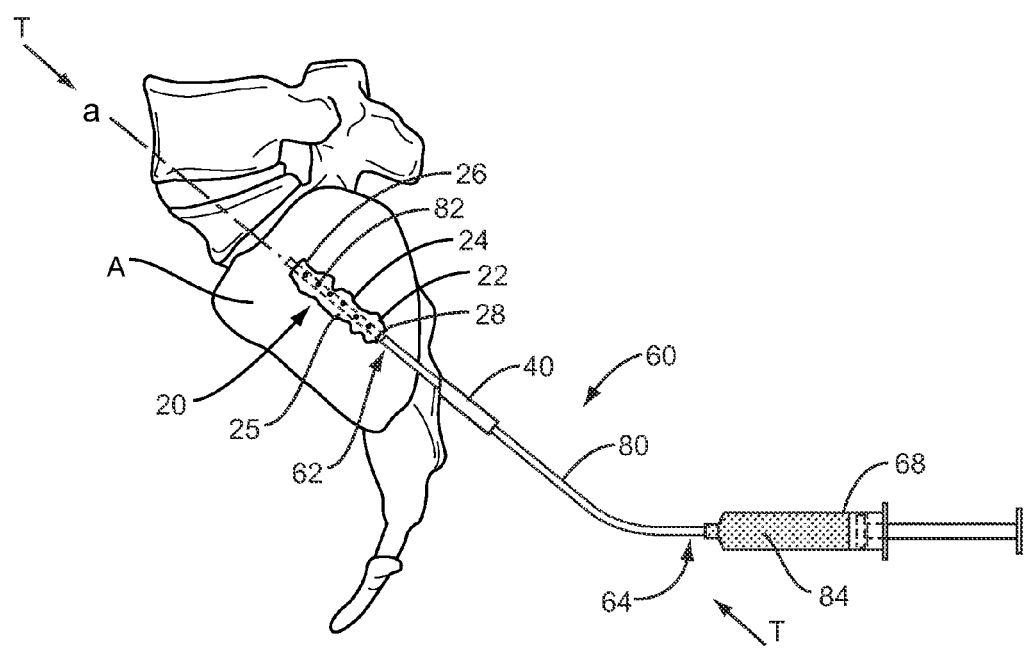
FIG. 2 is a side view of the implant system and the region shown in FIG. 1.
Figure 5:
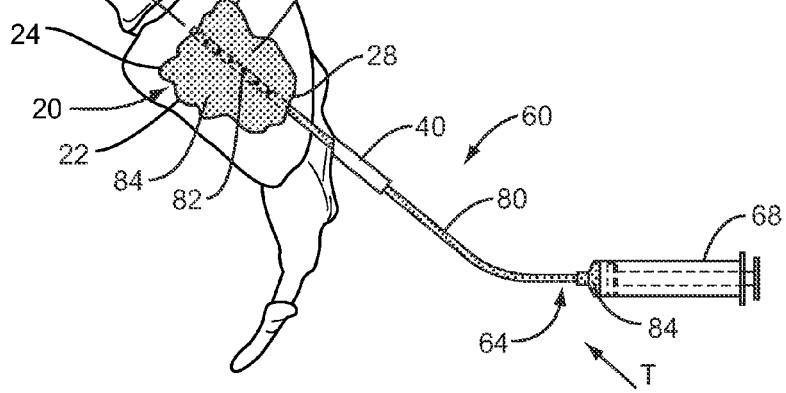
FIG. 5 is a side view of the implant system and the region shown in FIG. 4.
Figure 6:
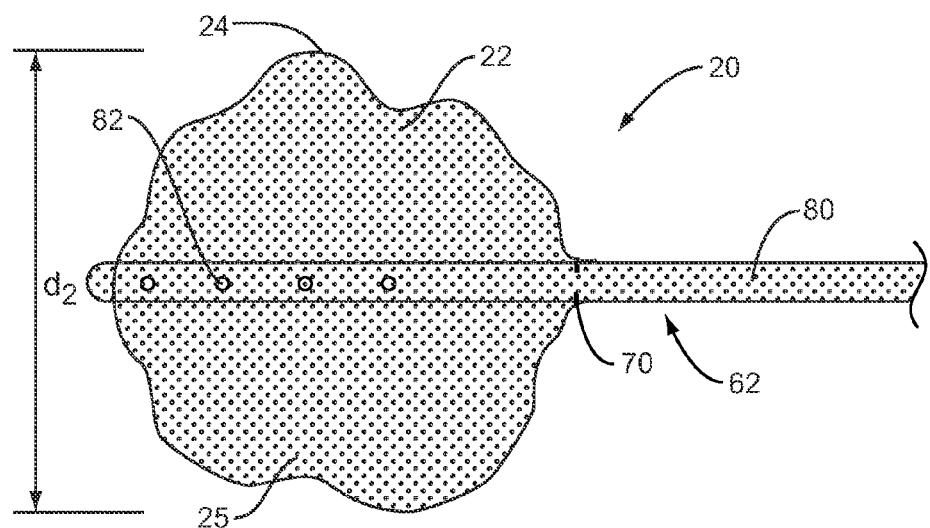
FIG. 6 is a side cutaway view, in part cross section, of the implant system shown in FIG. 4.

The implant system may be delivered using a trajectory, such as, for example, trajectories T shown in FIGS. 2 and 5, which are defined for insertion and/or injection of bodies 22 of sacro-iliac implants 20 within sacro-iliac joints J. Each implant 20 is inserted via the protected passageway along the defined trajectory T into sacro-iliac joints J. Each cavity of the respective sacro-iliac joints J are prepared along the respective trajectory for disposal of sacro-iliac implants 20. A guide wire, needle, probe and/or trocar-cannula assembly may be employed to penetrate tissues and create a pathway through the body of a patient to the sacro-iliac joint site for disposal of implants 20.

The protected passageway includes a delivery instrument 60 having a cannula 40 configured to deliver sacro-iliac implant 20 directly to the joint space of sacro-iliac joint J. Cannula 40 penetrates tissues and creates a pathway through the body of the patient to the sacro-iliac joint sites. It is envisioned that the dilator/delivery tube may include an endoscope camera tip for viewing insertion trajectory. It is further envisioned that delivery instrument 60 includes a sleeve that can be retracted for expansion of outer surface 24.

Sacro-iliac implant 20 is delivered to the joint space of sacro-iliac joint J and manipulated such that outer surface 24 of body 22 is disposed to compliantly engage opposing articular surfaces A, according to the contour of articular surfaces A. It is contemplated that body 22 may engage only one or a plurality of articular surfaces A. It is further contemplated that body 22 can be oriented for a preset, predetermined and/or guided to a predetermined orientation for disposal with articular surfaces A. In one embodiment, body 22 can be delivered to the joint space and then steered or rotated into a random or predetermined orientation. For example, body 22 and/or outer surface 24 can be disposed in the unexpanded orientation having a curvature, which straightens to a linear configuration as body 22 is delivered to the joint space through instrument 60. Body 22 and/or outer surface 24 returns to its original curvature upon exit from delivery instrument 60 at the joint space.

The implant system including sacro-iliac implant 20 is employed with a surgical arthroplasty procedure for treatment of sacro-iliac joint J of a patient using delivery instrument 60. Instrument 60 includes a distal portion 62 and a proximal portion 64. Distal portion 62 includes an expanding device, such as, for example, a high pressure catheter 80 detachably connected with implant body 22. Proximal portion 64 includes an injector 68 that fluidly communicates with catheter 80 for inflation of body 22. Injector 68 is actuated to provide the pressure required to expel a flowable and curable bio-compatible material, such as, for example, a bio-compatible material 84 from injector 68 through catheter 80 and into cavity 25 of outer surface 24 for inflation thereof.

Figure 7:
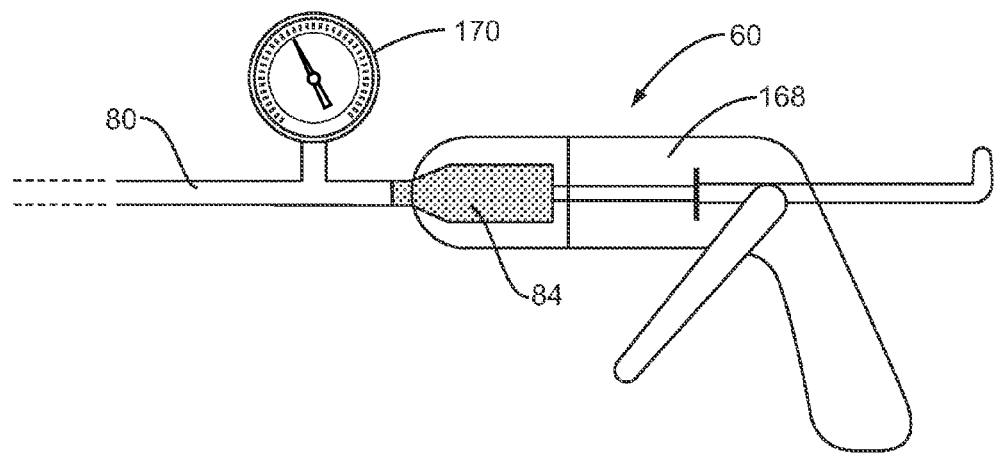
FIG. 7 is a side view of a delivery instrument of the implant system shown in FIG. 1.

It is contemplated that instrument 60 may employ various injectors for delivery of a flowable material to the expanding device such as, for example, a syringe, caulk gun, mechanical injector and/or power injector. It is further contemplated that instrument 60 may employ alternative pressure generating devices to inflate outer surface 24 such as a pump. In one embodiment as shown in FIG. 7, instrument 60 includes a mechanically assisted, material injector 168, such as, for example, a caulk gun configuration, and a pressure indicator 170 that provides visual indicia of the pressure of material 84 within body 22.

Figure 3:
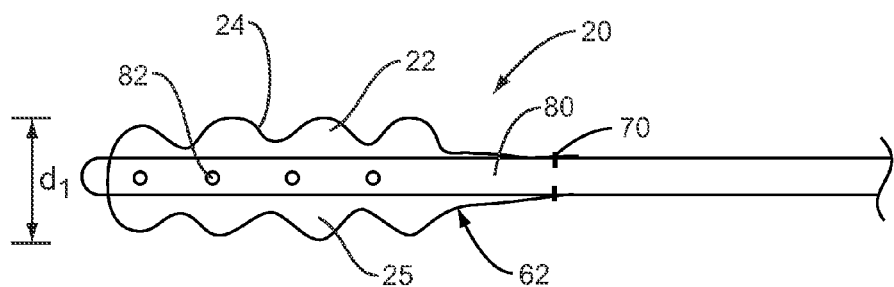
FIG. 3 is a side cutaway view, in part cross section, of the implant system shown in FIG. 1.

Outer surface 24 of body 22 is mounted with catheter 80 and disposed within the joint space of sacro-iliac joint J, as discussed. Outer surface 24 defines interior cavity 25 for disposal of catheter 80 therein. As shown in FIGS. 1 and 3, body 22 has first diameter $d_1$ and is disposed in the first, collapsed orientation.

Outer surface 24 includes elastically deformable walls attached with catheter 80 in a sealed engagement. The walls of outer surface 24 are configured to expand such that the volume of inner cavity 25 increases from the first orientation, an unexpanded configuration of body 22 having diameter $d_1$.

Catheter 80 includes a lumen through which material 84 is supplied through openings 82 to enlarge or inflate outer surface 24. Upon delivery of implant 20 to the surgical site, injector 68 is actuated via manual, mechanical and/or processor control element to force material 84 into cavity 25, which is thereby inflated to expand the walls of outer surface 24 in one or a plurality of directions, as described above, to dispose body 22 in the second, expanded orientation, as shown in FIGS. 4 and 5.

Outer surface 24 elastically deforms to compliant engagement with articular surfaces A. Body 22 is molded within the joint space of sacro-iliac joint J as outer surface 24 complies to articular surfaces A via delivery of material 84. Body 22 is filled with a sufficient amount of material 84, under a selected pressure from injector 68, to fill the targeted joint space of sacro-iliac joint J. Material 84 is allowed to cure and solidify under a maintained inflating pressure from injector 68 such that body 22 is molded in situ, as described above. It is contemplated that body 22 can be molded in situ such that body 22 is rigid, semi-rigid, flexible, compliant, solid inner core/flexible outer surface, flexible inner core/solid outer surface, porous, semi-porous, non-porous, permeable, semi-permeable and/or impermeable.

Catheter 80 is detached from outer surface 24 at a break off point 70. It is envisioned that catheter 80 is detachable from outer surface 24 via various structure and/or mechanisms, such as, perforations, weakened portions, threads, clips, pressure/friction fit and/or cut section, for separation of the component parts.

It is contemplated that catheter 80 can be rigid, semi-rigid, or flexible. It is further contemplated that catheter 80 can include one or a plurality of lumens to facilitate inflation with material 84. It is envisioned that body 22 in its expanded orientation can have various geometric shapes for compliance with articular surfaces A such as, for example, conical, frusto-conical, spherical, cubic, spherical, polygonal, ovoid, long conical, long spherical, rectangular, tapered, stepped, dog-bone shape, offset shapes and combinations thereof.

Outer surface 24 can be fabricated from any suitable material capable of withstanding the pressure supplied to enlarge or inflate outer surface 24 in situ, such as, for example, various polymeric materials, including polyethylene, polyethylene-terephthalates (PET), polyolefins, polypropylene, polyurethanes, silicone polyurethane co-polymers, nylon, polyvinyl chloride, silicone or other suitable material. It is envisioned that body 22 can be reinforced with woven or non-woven textile materials.

Catheter 80 is detached from outer surface 24 at break off point 70, as described above. Instrument 60 is removed from the surgical site. Sacro-iliac implant 20 remains disposed with sacro-iliac joint J for treating the sacro-iliac joint disorder. Body 22 is configured for compliant engagement with articular surfaces A. Body 22 engages and is movable to facilitate relative motion of articular surfaces A in a plurality of directions. It is contemplated that bodies 22 can slide or move relative to articular surfaces A allowing relative motion of the articular surfaces A of sacrum S and ilium I of sacro-iliac joint J. It is further contemplated that portions of outer surface 24 may be fixed with articular surfaces A while body 22 is disposed in a configuration to cushion the opposing articular surfaces A and facilitate relative motion of the opposing articular surfaces A. The outer surfaces of bodies 22 may be compressible.

Sacro-iliac implant 20 may include locking structure, such as, locking elements formed or attached with body 22, to facilitate fixation of outer surface 24 of body 22 within the joint space of sacro-iliac joint J. It is envisioned that such locking structure may include fastening elements such as, for example, clips, hooks, adhesives and/or flanges. Sacro-iliac implant 20 can be made of radiolucent materials such as polymers. Radiomarkers may be included for identification under x-ray, fluoroscopy, CT or other imaging techniques.

In one embodiment, as shown in FIGS. 8-11, sacro-iliac implant 20, similar to that described above, has a body 222. Body 222 is initially comprised of an injectable, bio-compatible material 284 that cures and solidifies such that body 222 is molded in situ to augment and provide stabilization to sacro-iliac joint J.

The material volume of body 222 is increased and configured for expansion within sacro-iliac joint J corresponding to the particular joint space and application parameters. The material volume of body 222 is increased and configured to expand from a first orientation (FIGS. 8 and 9), having an initial material volume, to a second orientation (FIGS. 10 and 11), having its material volume increased sufficiently for the particular augmentation application, whereupon the material of body 222 cures and is molded.

In the first orientation, an initial material volume is disposed within the joint space defined between articular surfaces A of sacro-iliac joint J. The initial material volume may be negligible, zero or a small volume. Material 284 is initially flowable so that it can be injected and/or extruded into the joint space.

Material 284 is injected into the joint space such that body 222 expands to the second orientation. Material 284 fills and occupies the joint space defined by articular surfaces A such that body 222 forms and is molded to a random configuration corresponding to the configuration of the defined joint space. Upon injection of a sufficient volume of material 284 in the defined joint space, body 222 forms in situ to dilate sacro-iliac joint J for augmentation and desired treatment, as described, and material 284 changes from a liquid to a relatively solid, non-flowable form having a significantly higher modulus of elasticity relative to the initially flowable form of material 284. It is contemplated that molding of body 222 in the second orientation can include setting, solidification, significantly increasing viscosity or modulus of elasticity, cross-linking, polymerization and/or vulcanization of material 284.

It is contemplated that this configuration of the implant system includes direct injection of material 284 into sacro-iliac joint J, which provides material penetration into crevices and/or fissures of articular surfaces A to improve support and bonding of body 222 with the joint surfaces.

In the second orientation, body 222 has an outer surface 224 defining its random configuration, corresponding to the configuration of the defined joint space, which engages opposing articular surfaces A of a sacro-iliac joint J. Body 222 is disposed within sacro-iliac joint J to space apart opposing articular surfaces A and treat sacro-iliac joint J. Outer surface 224 is compliant to a configuration of opposing articular surfaces A, as will be described, such that body 222 facilitates relative movement of opposing articular surfaces A. It is contemplated that outer surface 224 may be slidably engaged, fixed and/or releasably engageable with articular surfaces A. It is contemplated that the material volume of body 222 is expandable in one or a plurality of dimensions, such as, for example, height, width, length, diameter, radial direction and/or volumetric direction.

It is contemplated that articular surface A may refer to a sacral surface $S_1$ of a sacrum S and/or an iliac surface $I_1$ of an ilium I. Body 222 is configured to engage opposing articular surfaces such as sacral surface $S_1$ and iliac surface $I_1$ and/or opposing valleys or peaks of an individual sacrum S or ilium I. The material volume of body 222 may expand to a hollow, porous or cage configuration. Outer surface 224 is compliant to articular surfaces A and has a continuously even or smooth configuration. It is contemplated that outer surface 224 has a compliant configuration to substantially match articular surface(s) A and/or may be substantially smooth, rough, textured, spiked, porous, semi-porous, dimpled, keeled and/or polished. It is further contemplated that the volumetric dimension of body 222 may include solid, partially solid, rigid, semi-rigid, flexible, semi-permeable, permeable, non-permeable, porous, non-porous and/or semi-porous portions.

Body 222 may include injectable, flowable and curable bio-compatible materials, such as, for example, fluid precursors to tissue adhesives, albumin (for example, BioGlue® manufactured by CryoLife Inc. of Kennesaw, Ga.), cyanoacrylate adhesives, bio-compatible adhesives, polyvinyl alcohol hydrogels, hydrogel compositions, polydimethylsiloxanes, silicones, polyurethanes, silicone-polyurethane copolymers, synthetic rubbers or elastomers, epoxy, PMMA, hyaluronic acid, collagen, silicone based materials, silk-elastin, protein based materials or polymers and/or combinations thereof. It is contemplated that molding of body 222 via curing and/or solidification of material 284 in situ is facilitated via physical elements, chemical elements including liquid-solid phase transition, hydrogen bonding, polymerization and/or cross-linking.

This configuration of body 222 facilitates disposal of body 222 within a sacro-iliac joint, such that, for example, body 222 separates articular surfaces A to dilate the sacro-iliac joint, facilitate relative movement of opposing articular surfaces A, and/or prevent joint surfaces from undesired engagement such as that caused by degeneration and cartilage wear. It is contemplated that such spacing apart of the articular surfaces of the sacro-iliac joint with compliant, moldable body 222, tensions ligaments, supports the sacro-iliac joint and restores motion of the sacro-iliac joint.

Alternative to the random configuration of body 222 in the second orientation corresponding to the configuration of the defined joint space described above, it is envisioned that the overall and/or cross-sectional geometry of expanded body 222 may have various configurations, for example, round, oval, oblong, triangular, rectangular, polygonal, irregular, uniform, non-uniform, consistent or variable, according to the geometry of the joint space disposed between the articular surfaces and/or the requirements of a particular implant system application. It is further envisioned that the thickness and/or diameter of body 222 may be varied depending on whether a sacro-iliac joint is drilled and/or tapped before insertion of an implant.

Body 222 can be expanded to various configurations and dimensions with regard to size, shape, thickness, geometry and material. Body 222 may also be formed of one or a plurality of elements such as spaced apart portions, staggered patterns and mesh. It is envisioned that the particular geometry and material parameters of body 222 may be selected to modulate the flexibility or stiffness of sacro-iliac implant 20, such as those examples discussed herein. For example, body 222 can be configured to have varying ranges or degrees of flexibility or stiffness such as resilient, rigid, compliant, or reinforced. Depending on the flexibility or stiffness of body 222, the flexibility or stiffness of sacro-iliac implant 20 can be contoured according to the requirements of a particular application.

In one embodiment, body 222 may be molded in situ to include one or a plurality of cavities, which may partially extend or completely extend through body 222. Such cavities can be oriented with body 222 to face articular surfaces A, sacral surface $S_1$ and iliac surface $I_1$. It is further envisioned that the cavities may include through holes, slots, voids, indentations, and/or non-interference configurations and dimensions. In one embodiment, body 222 and the cavities described above may be configured to expel and/or elute at least one agent therefrom, similar to that described above with regard to body 22.

In one embodiment, the implant system includes a plurality of bodies 222, described above, in each or both sacro-iliac joints. It is contemplated that employing the plurality of bodies 222 can optimize the amount sacro-iliac joint J can be spaced apart such that a joint space dimension can be preselected. The material volume for each of the plurality of bodies 222 can be inserted through the same or an alternate trajectory. The plurality of bodies 222 can be oriented in a side-by-side engagement, spaced apart and/or staggered. It is envisioned that the material volume for each of one or all of the plurality of bodies 222 may be inserted via a trajectory oriented from an anterior, posterior, superior or inferior direction, similar to that described herein. It is further envisioned that one or a plurality of bodies 222 may be used.

In assembly, operation and use, sacro-iliac implant 20 including body 222 is employed with a surgical arthroplasty procedure for treatment of an applicable condition or injury of an affected sacro-iliac joint J, as shown in FIGS. 8-11. It is contemplated that the implant system is inserted with sacro-iliac joint J to space apart articular joint surfaces, establish joint tension, provide support and relative motion of the articular surfaces of sacro-iliac joint J in a less invasive approach for treatment. It is further contemplated that the implant system is inserted with a sacro-iliac joint J as a sacro-iliac joint spacer to restore ligamentous tension, eliminate painful motion, and/or preserve and restore motion and/or separate and cushion opposing articulating surfaces. It is envisioned that the implant system may maintain joint tension without promoting bone growth.

In use, to treat the affected section of sacro-iliac joint J, a medical practitioner obtains access to a surgical site including sacro-iliac joint J in any appropriate manner, such as through incision and retraction of tissues, similar to that described above with regard to body 22. In one embodiment, a minimally invasive approach is employed such that a small gauge hypodermic needle or a small diameter cannula penetrates tissue and a tip thereof is disposed within a targeted joint space. Material 284 is injected in the joint space to form body 222, as described.

Figure 9:
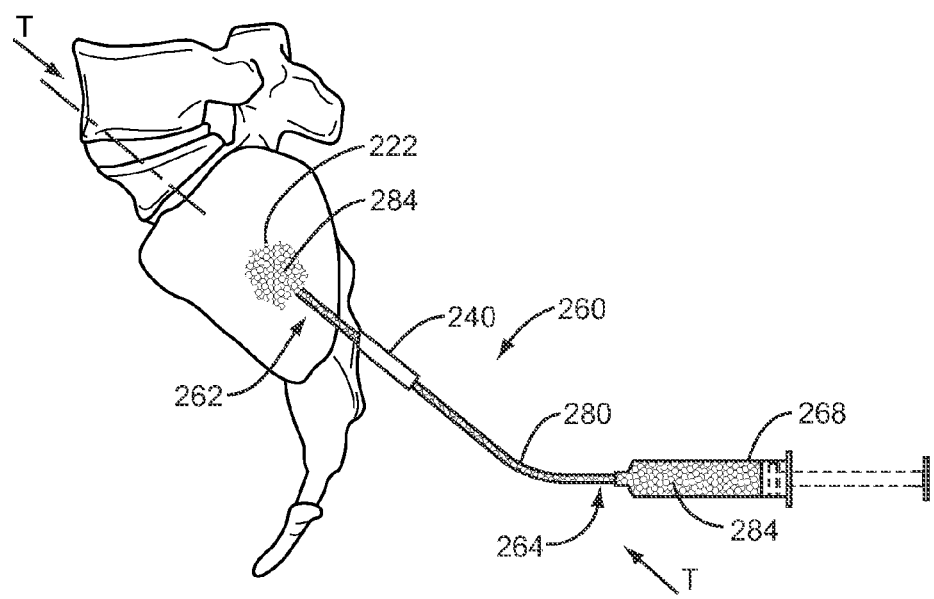
FIG. 9 is a side view of the implant system and the region shown in FIG. 8.
Figure 11:
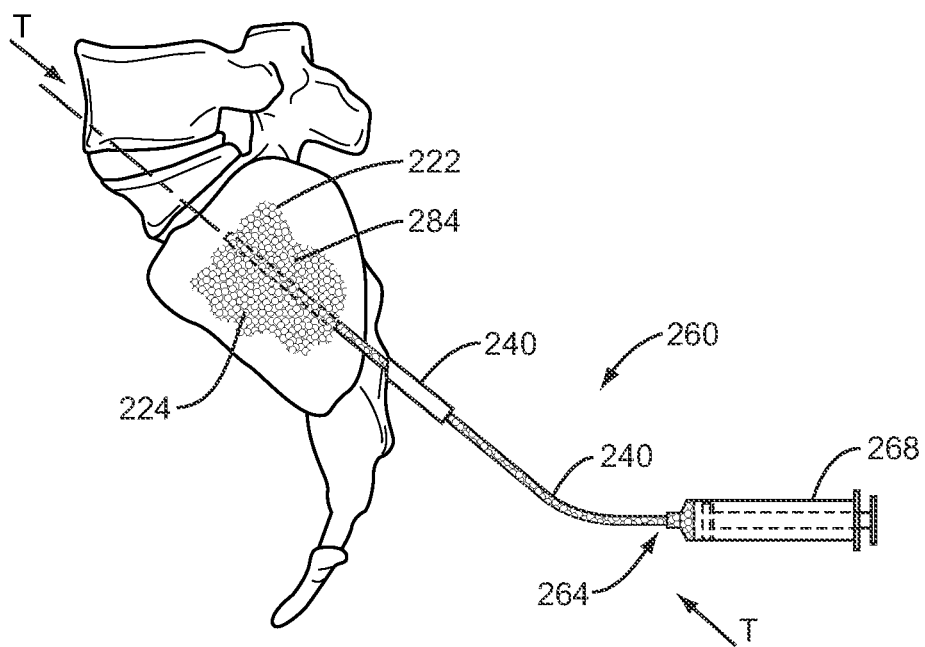
FIG. 11 is a side view of the implant system and the region shown in FIG. 10.

The implant system may be delivered using a trajectory, such as, for example, trajectories T shown in FIGS. 9 and 11, which are defined for random insertion and/or injection of material 284, as described above, which will form randomly configured bodies 222 within sacro-iliac joints J corresponding to the configuration of the defined joint space. Material 284 is delivered via the protected passageway along the defined trajectory T into sacro-iliac joints J. Each cavity of the respective sacro-iliac joints J is prepared along the respective trajectory for disposal of sacro-iliac implants 20. A guide wire, needle, probe and/or trocar cannula assembly may be employed to penetrate tissues and create a pathway through the body of a patient to the sacro-iliac joint site for disposal of implants 20.

The protected passageway includes a delivery instrument 260 having a small diameter cannula 240 with a needle tip configured to deliver material 284 directly to the joint space of sacro-iliac joint J. Cannula 240 penetrates tissues and creates a pathway through the body of the patient to the sacro-iliac joint sites. It is envisioned that delivery instrument 260 may include a sleeve that can be retracted for expulsion of material 284.

Material 284 is delivered to the joint space of sacro-iliac joint J such that body 222 is formed in the second orientation, as described above. Upon molding in situ, body 222 is flexible and outer surface 224 is disposed to compliantly engage opposing articular surfaces A, according to the contour of articular surfaces A. It is contemplated that body 222 may engage only one or a plurality of articular surfaces A. It is further contemplated that body 222 can be disposed in a predetermined orientation and/or injection of material 284 guided to a predetermined orientation for disposal with articular surfaces A.

The implant system including sacro-iliac implant 20 is employed with a surgical arthroplasty procedure for treatment of sacro-iliac joint J of a patient using delivery instrument 260. Instrument 260 includes a distal portion 262 and a proximal portion 264. Distal portion 262 includes a high-pressure catheter 280 configured to deliver material 284 to sacro-iliac joint J through cannula 240. Proximal portion 264 includes an injector 268 that fluidly communicates with cannula 240 for pressurized injection of material 284. Injector 268 is actuated to provide the pressure required to expel material 284 from injector 268 through catheter 280 and cannula 240, into the joint space between opposing articular surfaces A for expansion of body 222 from the first orientation.

Figure 8:
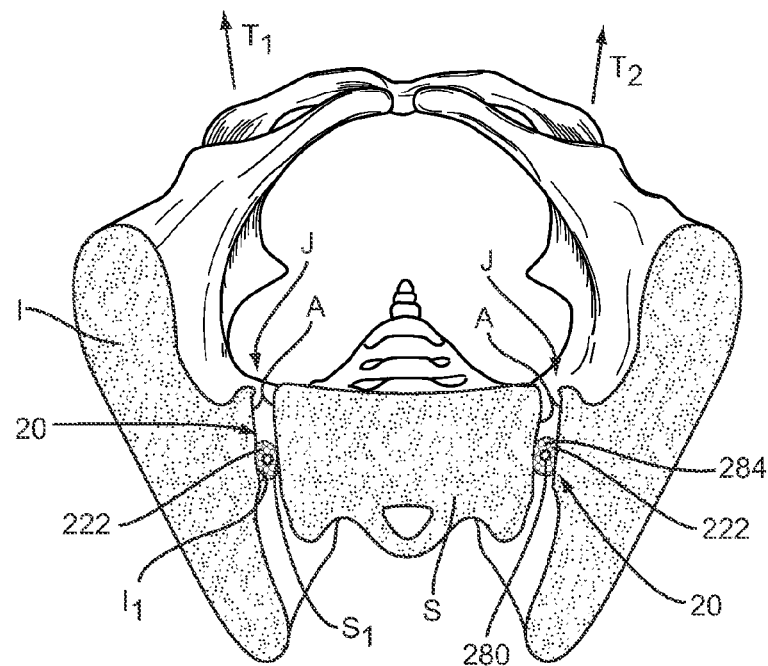
FIG. 8 is a plan view, in part cross section, of one embodiment of an implant system in accordance with the principles of the present disclosure and a sacro-iliac/ilio-pelvic region.
Figure 10:
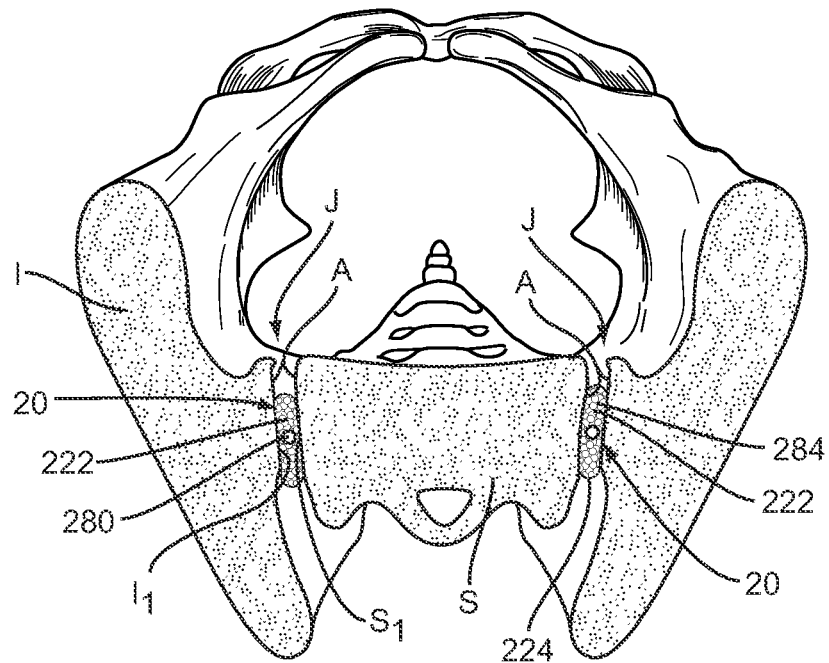
FIG. 10 is a plan view, in part cross section, of the implant system and the region shown in FIG. 8.

As shown in FIGS. 8 and 9, body 222 is disposed in the first orientation such that body 222 is comprised of an initial material volume. Catheter 280 includes a lumen through which material 284 is supplied through the tip of cannula 240 adjacent distal end 262 to form body 222. Injector 268 is actuated to force material 284 into the joint space and between opposing articular surfaces A, as described above, to dispose body 222 in the second orientation having an increased material volume sufficient for an augmentation application, as shown in FIGS. 10 and 11. It is contemplated that material 284 may penetrate crevices and/or fissures of the articular surfaces A.

Material 284 is injected for compliant engagement with articular surfaces A. Body 222 is molded to a random configuration corresponding to the defined joint space of sacro-iliac joint J and outer surface 224 is formed and complies to articular surfaces A. Body 222 is formed with a sufficient amount of material 284, under a selected pressure from injector 268, to occupy the targeted joint space of sacro-iliac joint J. Material 284 is injected and thereafter allowed to cure and solidify, as described above, such that body 222 is molded in situ. It is contemplated that body 222 can be molded in situ such that body 222 is rigid, semi-rigid, flexible, compliant, solid inner core/flexible outer surface or flexible inner core/solid outer surface.

Catheter 280 and cannula 240 are detached from molded body 222. It is envisioned that cannula 240 is detachable from body 222 via various structure and/or mechanisms, such as, removal or detachment of cannula 240 prior to final molding, via perforations, weakened portions and/or cut section. It is contemplated that catheter 280 can include one or a plurality of lumens to facilitate delivery of material 284. It is further contemplated that body 222 in its second orientation can have various geometric shapes for compliance with articular surfaces A.

Instrument 260 is removed from the surgical site. Body 222 of sacro-iliac implant 20 remains disposed with sacro-iliac joint J for treating the sacro-iliac joint disorder. Outer surface 224 is configured for compliant engagement with articular surfaces A. Body 222 engages and is movable to facilitate relative motion of articular surfaces A in a plurality of directions. It is contemplated that bodies 222 can slide or move relative to articular surfaces A allowing relative motion of the articular surfaces A of sacrum S and ilium I of sacro-iliac joint J. It is further contemplated that portions of outer surface 224 may be fixed with articular surfaces A while body 222 is disposed in a configuration to cushion the opposing articular surfaces A and facilitate relative motion of the opposing articular surfaces A. The outer surfaces of bodies 222 may be compressible.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A sacro-iliac implant system comprising:
   an instrument extending between opposite first and second ends and comprising an intermediate section therebetween; and
   at least one implant including a body extending between opposite proximal and distal ends, the proximal end engaging the intermediate section and the distal end engaging the second end, the body defining an outer surface and being disposed to space apart opposing articular surfaces of a sacro-iliac joint, wherein the body includes at least one agent and is engageable with the opposing articular surfaces and the outer surface is compliant to a configuration of the opposing articular surfaces such that the body facilitates relative movement of the opposing articular surfaces;
   wherein the body expands from a first, collapsed orientation having a first diameter to a second expanded orientation having a second diameter, the second diameter being 2 to 10 times greater than the first diameter, the body being pre-formed to have a non-uniform shape when the body is in the second orientation and no external force is applied to the outer surface.

2. A sacro-iliac implant system according to claim 1, wherein the body is expandable in a configuration to space apart the opposing articular surfaces.

3. A sacro-iliac implant system according to claim 1, wherein the outer surface is compliant to a configuration of the opposing articular surfaces such that the body is moldable in situ to the configuration of the opposing articular surfaces.

4. A sacro-iliac implant system according to claim 1, wherein the outer surface is compliant to a configuration of the opposing articular surfaces such that the body is moldable in situ to the configuration of the opposing articular surfaces when the body is in the second orientation.

5. A sacro-iliac implant system according to claim 1, wherein the body is an injectable, bio-compatible material that is moldable in situ to a configuration of the opposing articular surfaces.

6. A sacro-iliac implant system according to claim 1, wherein the body is moldable such that the outer surface is flexible.

7. A sacro-iliac implant system according to claim 1, wherein the body is expandable in a configuration to space apart the opposing articular surfaces and expansion of the body includes inflating the body with a fluid.

8. A sacro-iliac implant system according to claim 7, wherein the outer surface of the body is elastically deformable and the fluid is a curable, bio-compatible material.

9. A sacro-iliac implant system according to claim 7, wherein the body is inflated with a in situ curable, bio-compatible material.

10. A sacro-iliac implant system according to claim 1, wherein the at least one implant includes a plurality of implant bodies.

11. A sacro-iliac implant system according to claim 1, wherein the instrument is configured to deliver the implant to the sacro-iliac joint and the proximal end includes perforations such that the body is detachably connected to the instrument.

12. A sacro-iliac implant system according to claim 1, wherein the instrument is configured to deliver the implant to the sacro-iliac joint and is configured to deliver a curable, bio-compatible material to the body for inflation thereof, the system further comprising a clip positioned over the proximal end and the intermediate section to removably couple the proximal end to the instrument.

13. A sacro-iliac implant system comprising:
a bio-compatible material;
at least one implant including a body extending between opposite proximal and distal ends, the body defining an outer surface and being configured to engage and space apart opposing articular surfaces of a sacro-iliac joint to facilitate relative movement of the opposing articular surfaces, the body including at least one biologically-active agent and being configured to expand from a first, collapsed orientation having a first diameter to a second inflated orientation having a second diameter that is 2 to 10 times greater than the first diameter, the body being pre-formed to have a non-uniform shape when the body is in the second orientation and no external force is applied to the outer surface, the outer surface being compliant to a configuration of the opposing articular surfaces such that the body is inflated with a fluid and moldable in situ to the configuration of the opposing articular surfaces; and
a delivery instrument extending between opposite first and second ends and comprising an intermediate section therebetween, the instrument being configured to deliver the fluid to the body, the distal end engaging the second end and the proximal end engaging the intermediate section such that the instrument is detachably connected with the body.

14. A sacro-iliac implant system according to claim 13, wherein the fluid is a curable, bio-compatible material.

15. A sacro-iliac implant system according to claim 1, wherein the body includes locking structures formed or attached with the body to facilitate fixation of the outer surface within a joint space of the sacro-iliac joint.

16. A sacro-iliac implant system according to claim 1, wherein the at least one agent is an anti-inflammatory drug that reduces signs of inflammation.

17. A sacro-iliac implant system according to claim 1, wherein the second end extends beyond the distal end.

18. A sacro-iliac implant system according to claim 1, wherein the instrument comprises a plurality of openings between the intermediate section and the second end.

19. A sacro-iliac implant system according to claim 18, wherein the first end comprises an injector that injects an in situ curable, bio-compatible material into the implant through the openings under an inflation pressure and maintains the inflation pressure as the in situ curable, bio-compatible material cures within the implant.

20. A sacro-iliac implant system according to claim 1, wherein the body comprises polyethylene.

* * * * *